US008355876B2

(12) United States Patent
Prabhakarpandian et al.

(10) Patent No.: US 8,355,876 B2
(45) Date of Patent: *Jan. 15, 2013

(54) MICROFLUIDIC ASSAY FOR SELECTION AND OPTIMIZATION OF DRUG DELIVERY VEHICLES TO TUMORS

(75) Inventors: Balabhaskar Prabhakarpandian, Madison, AL (US); Kapil Pant, Madison, AL (US); Shivshankar Sundaram, Tampa, FL (US)

(73) Assignee: CFD Research Corporation, Huntsville, AL (US)

( * ) Notice: Subject to any disclaimer, the term of this patent is extended or adjusted under 35 U.S.C. 154(b) by 309 days.

This patent is subject to a terminal disclaimer.

(21) Appl. No.: 12/648,296

(22) Filed: Dec. 28, 2009

(65) Prior Publication Data

US 2010/0099136 A1   Apr. 22, 2010

Related U.S. Application Data

(63) Continuation-in-part of application No. 11/393,715, filed on Mar. 31, 2006, now Pat. No. 7,725,267.

(51) Int. Cl.
*G01N 33/48* (2006.01)
(52) U.S. Cl. .......................................................... 702/19
(58) Field of Classification Search ................ 702/19
See application file for complete search history.

(56) References Cited

U.S. PATENT DOCUMENTS

2002/0160505 A1   10/2002   Groves et al.
2006/0154361 A1*   7/2006   Wikswo et al. ............ 435/289.1

FOREIGN PATENT DOCUMENTS

WO   2004020341 A2   3/2004

OTHER PUBLICATIONS

Tan et al., "Microfluidic Patterning of Cellular Biopolymer Matrices for Biomimetic 3-D Structures." Biomedical Microdevices (2003) 5(3):235-244.
Runyon et al., "Minimal Functional Model of Hemostasis in a Biomimetic Microfluidic System" Angew. Chem. Int. Ed. (2004) 43:1531-1536.
Shevkoplyas et al. Microvascular Research (2003) 65:132-136.

* cited by examiner

*Primary Examiner* — Jerry Lin
(74) *Attorney, Agent, or Firm* — Maschoff Gilmore & Israelsen (57) ABSTRACT

An apparatus and method for assaying a tumor drug delivery vehicle comprises a synthetic microvascular network of interconnected flow channels in fluid communication through a porous wall with a tissue space containing animal cells and means for quantifying drug delivery from the microvascular network to the animal cells.

30 Claims, 11 Drawing Sheets

Symmetric Diameter, Symmetric Angle

FIG. 11

MICROFLUIDIC ASSAY FOR SELECTION AND OPTIMIZATION OF DRUG DELIVERY VEHICLES TO TUMORS

CROSS-REFERENCE TO RELATED APPLICATIONS

This application claims priority under 35 U.S.C. 120 to application Ser. No. 11/393,715, filed Mar. 31, 2006.

STATEMENT REGARDING FEDERALLY SPONSORED RESEARCH

The U.S. Government may have certain rights in this invention pursuant to Contract Number 1R43CA139841-01 awarded by the National Institutes of Health.

BACKGROUND OF THE INVENTION

1. Field of the Invention

The present invention relates to microfluidic devices and assay methods for the selection and optimization of vehicles for drug delivery to tumors.

2. Description of Related Art

Existing in-vitro tumor drug delivery models are often poor predictors of drug delivery to tumors. Simple in-vitro models cannot accurately capture complex phenomenon involved in tumor drug delivery, which are affected by the physicochemical properties drugs and delivery vehicles and complex tumor microvasculature. Tumor microvasculature is substantially different from that found in normal tissue. For example, interstitial pressures are higher in solid tumors than in normal tissues and tumor microvasculature often has higher vascular permeability than normal microvasculature. Such factors should be accounted for by in-vitro models used to accurately evaluate potential drug delivery vehicles.

BRIEF SUMMARY OF THE INVENTION

The present invention provides methods and apparatus for screening tumor drug delivery vehicles that accounts for the geometric and flow properties, increased permeability, and higher interstitial pressures of tumor microvasculature. The apparatus includes a microfluidic device comprising an optically clear microfluidic chip containing a microvascular network of interconnected flow channels having dimensions from 10-500 μm in cross-section. The luminal surfaces of the flow channels are coated with a confluent layer of cultured endothelial cells and mimic physiological microvascular environments. Tumor cells are cultured in extravascular tissue spaces surrounded by the flow channels. The microchannels are separated from the tissue space by pores in the walls of the channels having dimensions in the range of 0.2-5 μm to represent leaky vessels that allow transport of delivery vehicles across vascular walls and into the tissue spaces. Candidate drug delivery vehicles are introduced into and flowed through the flow channels of the device at physiologically realistic flow rates and shear forces. The ability of candidate drug delivery vehicles to reach and/or permeate cultured tumor cells and/or to transfect tumor cells, for example, may be used to select for and/or optimize the performance of the drug delivery vehicle.

DETAILED DESCRIPTION OF THE INVENTION

Definitions

A "synthetic microvascular network" (SMN) is a man made network comprising interconnected, nonlinear flow channels that form geometrical features and have fluid flow properties found in physiological microvascular networks. The flow channels (synthetic vessels) form intersecting networks and may be arranged end to end, analogous to an arteriole, capillary, venule sequence. Flow channels and the SMNs they form possess geometric characteristics of physiological microvascular including variable cross-sectional shapes, variable cross-sectional areas, convolutions, turns, and/or anastomoses. A network of linear channels joining at angles, for example, is not an SMN because such a network possesses geometrical shapes and produced flow characteristics not found in physiological microvascular networks. Straight channels or other channels having non-physiological geometries may be used to link a synthetic microvascular network to other components of a microfluidic chip. These channels, however, are not a part of the microvascular network. One or more flow channels of a SMN may comprise porous walls such that liquid may move from the interior (lumen) of the flow channel into a space external to the lumen in a manner similar to the movement of fluid from the lumen of a physiological vessel into an interstitial space.

An Idealized microvascular network (IMN) is a man made network comprising interconnected flow channels that have certain fluid flow properties found in physiological microvascular networks. The diameters of the channels range from 10-500 μm and comprise of angles typically between 15° and 135°. One or more flow channels of an IMN may comprise porous walls such that liquid may move from the interior (lumen) of the flow channel into a space external to the lumen in a manner similar to the movement of fluid from the lumen of a physiological vessel into an interstitial space.

As used herein, the term "idealized" in association with a microfluidic network, junction, or bifurcation is used to describe a synthetic network, junction, or bifurcation consisting of straight microfluidic channels joined at acute, right, or obtuse angles.

As used herein, a microfluidic channel may have a rectangular, circular, semi-circular, irregular or a combination of cross-sectional shapes. The dimensions of a channel are described, for example, by length, depth and width wherein the depth is measured perpendicular to the plane of a microfluidic chip containing the channel and length and width are measured in directions lying in the plane of the microfluidic chip containing the channel. Channels having circular or semi-circular cross-sections may be described as having variable depth and width relative to channels having rectangular cross-sections or may alternatively be described in terms of channel diameter. Maximum depth and width when used to describe a channel having a circular or semi-circular cross-section are both equal to the maximum diameter of the channel. When used to describe a channel having a rectangular cross-section, the maximum width and depth refer to the constant width and depth of a channel having a constant width and depth or to the highest values for width and depth for channels having variable width and depth.

A microfluidic chip is constructed using techniques employed in the semiconductor industry such as photolithography, wet chemical etching, thin film deposition and soft lithography using polymeric substrates, such as Polydimethylsiloxane (PDMS). Other materials that may be used in place of PDMS include Poly(Styrene Butadiene Styrene) (SBS) and Poly(Styrene-Ethylene-Butadiene-Styrene) (SEBS) elastomers, Polyester-ether (PEE) thermoplast, and thermoset polyester (TPE), which can be used for replica molding fabrication techniques. Polyolefin plastomer (POP's) can be specifically used for submicron range channels. Glass or quartz with reactive wet/dry etching of the microchannels can also be used. Thermoplastic materials such as polymethylmethacrylate (PMMA), polycarbonate (PC), cyclic olefin copolymer (COC), polystyrene (PS), poly vinyl chloride (PVC), and polyethylene terephthalate glycol (PETG) can be used with embossing techniques or injection molding. PS, PC, cellulose acetate, polyethylene terephthalate (PET), PMMA, PETG, PVC, PC, and polyimide can also be used with laser ablation techniques. In general, a microfluidic chip is formed with a number of microchannels that are connected to a variety of reservoirs containing fluid materials. The fluid materials are driven or displaced within these microchannels throughout the chip using electrokinetic forces, pumps and/or other driving mechanisms.

"Tortuosity" is a measure of the indirectness of a vessel or flow channel path. Tortuosity can be measured in several ways. One exemplary means of measuring tortuosity is to sum the angles between consecutive trios of points along the space curve represented by a vessel skeleton and then normalize by path length. Tortuosity may also be measured, for example, by counting inflection points along each vessel or flow channel and multiplying this number (plus one) times the total path length and then dividing by the distance between the ends of the each vessel or flow path.

Tumor cells, as used herein, includes primary and cultured neoplastic cells derived from naturally occurring or artificially induced tumors, as well as normal cells transformed with exogenous nucleic acid to produce neoplastic cell lines.

Figure 1:
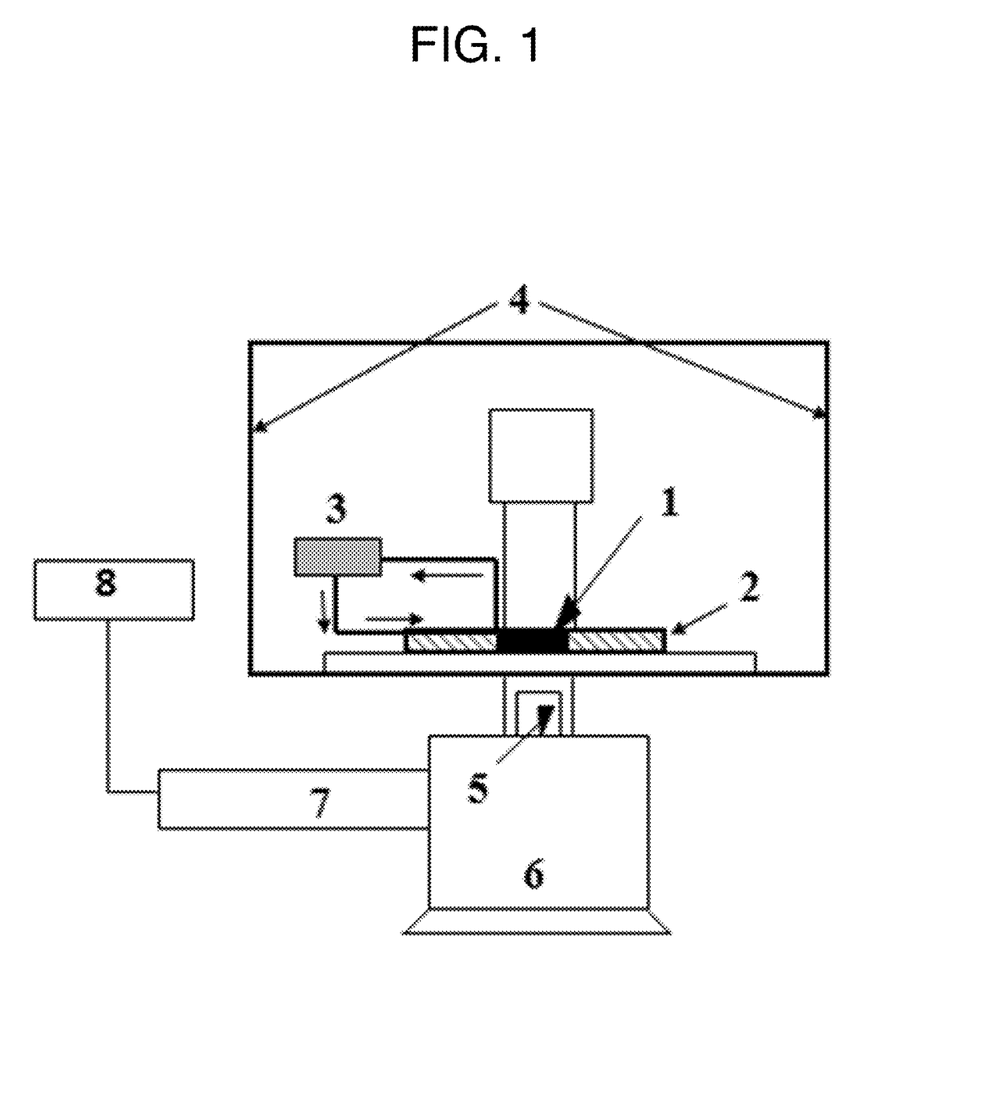
FIG. 1 is a drawing showing the components of a system used for screening tumor drug delivery vehicles.

Assay System:

FIG. 1 shows a non-limiting example of a system for performing tumor drug delivery vehicle screening assays according to the present invention. The system comprises a pumping means (3) such as a peristaltic pump (for recirculation/multiple pass) or a syringe pump (single pass) to move fluids through microfluidic channel networks. For experiments with a peristaltic pump, a microfluidic chip (1) is placed on an automated stage device (2) and connected to a pump (3) that is connected to inlets, outlets, and, optionally, ports on the microfluidic chip (1). The microfluidic chip (1) is preferably contained within an incubation chamber (4) and is positioned over an objective lens (5) of a brightfield, phase contrast or fluorescent microscope (6). Optical means such as a CCD camera or video camera (7) are used to visualize cells within the microfluidic chip (1). The camera (7) is in communication with a computer (8) for data collection and control of microscope (6), camera (7), and the microscope mounted accessories. For experiments with a syringe pump, the syringe pump (3) is connected to the microfluidic chip (1) and fluid leaving the microfluidic chip (1) is sent to waste (not shown).

Figure 2:
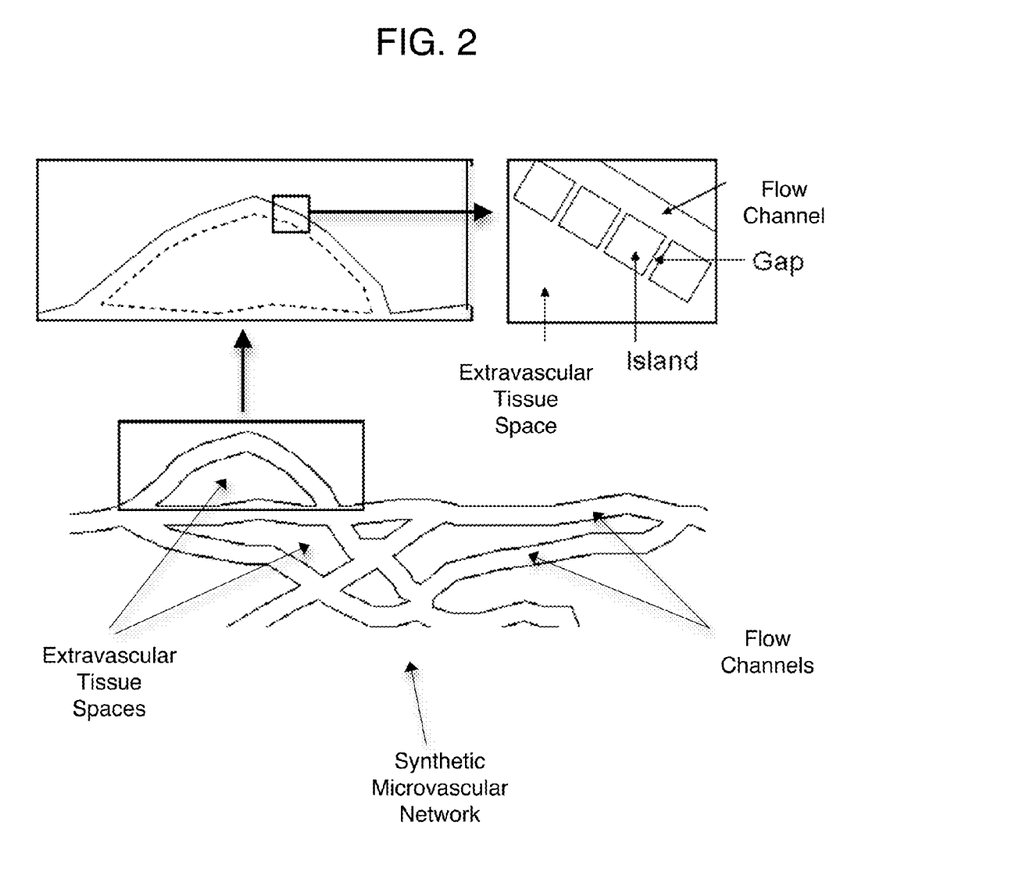
FIG. 2 is a drawing showing a SMN on a microfluidic chip.

Microfluidic Chips:

The microfluidic chips used in the assay system may comprise one or more SMNs, one or more IMNs, or a combination of SMNs and IMNs. FIG. 2 shows several views of a SMN in a microfluidic chip according to the invention. The SMN is made of interconnected nonlinear flow channels that form a geometry that provides physiological flow conditions including convective flow and diffusion. The geometry of the SMN is derived from one or more images of one or more in-vivo microvascular networks. The SMN comprises extravascular tissue spaces separated from the lumen of flow channels by porous walls that allow liquid to diffuse from the flow channels into the tissue spaces. The tissue spaces preferably have cross-sectional luminal dimensions of between 100 μm and 1 cm. In this example, the walls of flow channels surrounding the tissue spaces are constructed with 0.2-5 μm wide gaps to allow liquid diffusion. The portions of the walls of the flow channels between gaps are referred to as islands.

The tissue spaces in a SMN or an IMN preferably comprise a port that serves as an inlet and an outlet for introducing fluid and cells into the tissue spaces and for removing liquid and cells from the tissue spaces. Tissue spaces may also have separate inlets and outlets. The pressure inside each tissue space is preferably regulated through an inlet/outlet port or through a dedicated pressure valve. The walls of at least some of the flow channels that also form the walls of a tissue space are porous to liquids such as aqueous buffers to allow diffusion from the lumen of the microvascular network into the lumen of the tissue space. Porosity may be achieved, for example, by way of gaps, perforations, and/or pores present in the walls of the flow channels. The walls of the flow channels may preferably be coated with a confluent layer of primary or cultured endothelial cells. This may be facilitated by first coating the walls of the flow channels with basement matrix such as Matrigel®, collagen, or other extracellular matrix (ECM) components.

Figure 3:
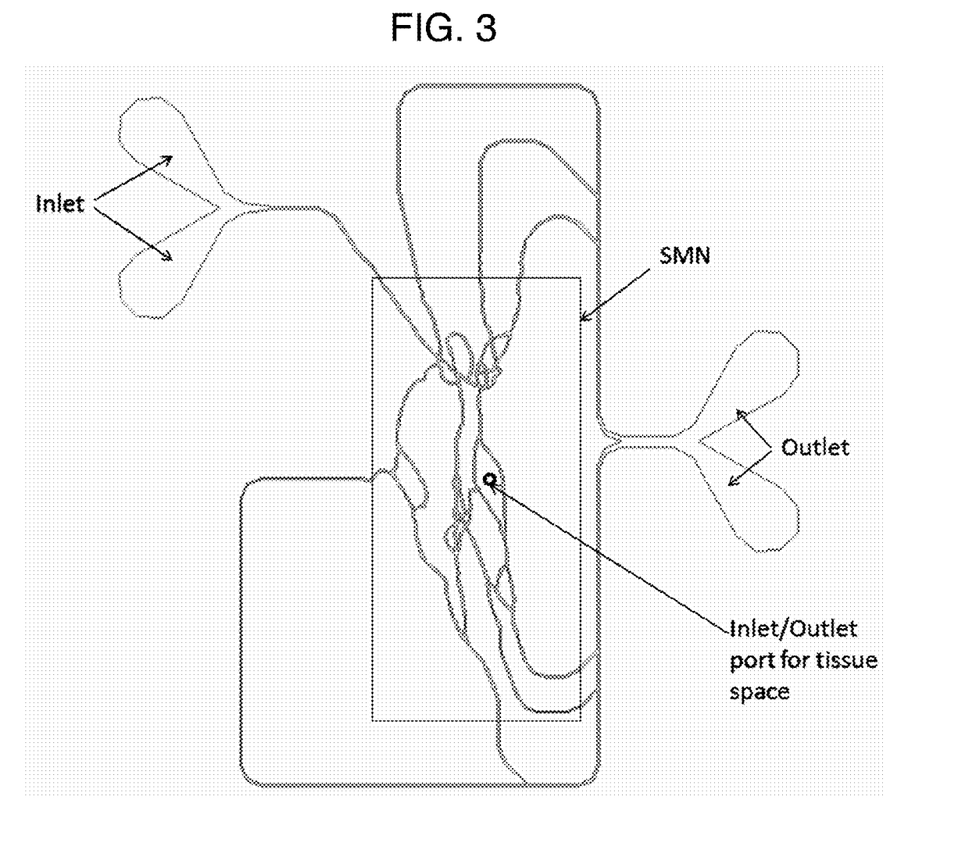
FIG. 3 is a drawing showing the components of a microfluidic chip for screening tumor drug delivery vehicles using a SMN.

FIG. 3 shows an example of a microfluidic chip comprising a SMN. The SMN comprises one or more tissue spaces containing a port that serves as an inlet into and an outlet from the tissue space. The SMN is in fluid communication with an inlet and an outlet via microfluidic channels connected to nonlinear flow channels in the SMN.

Figure 4:
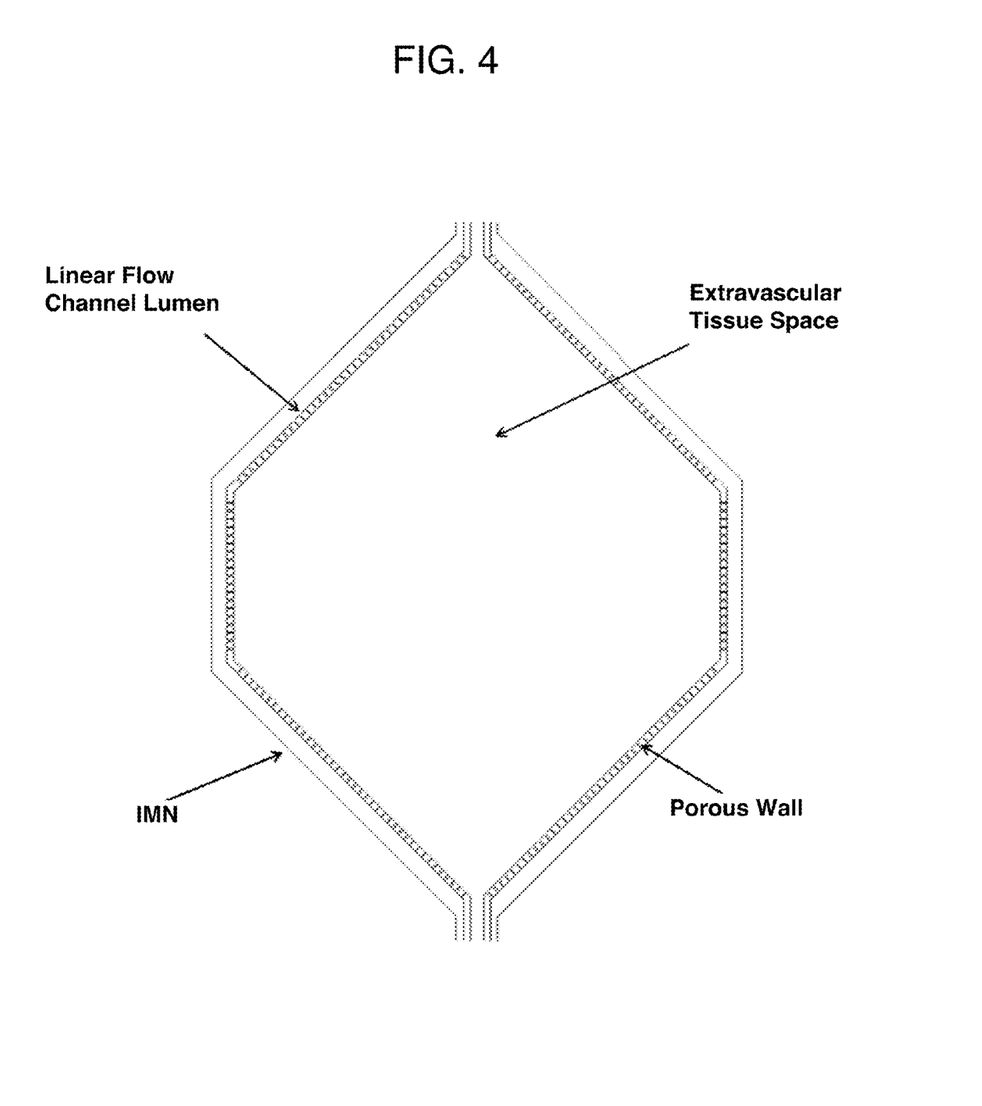
FIG. 4 is a drawing showing an IMN on a microfluidic chip.
Figure 5:
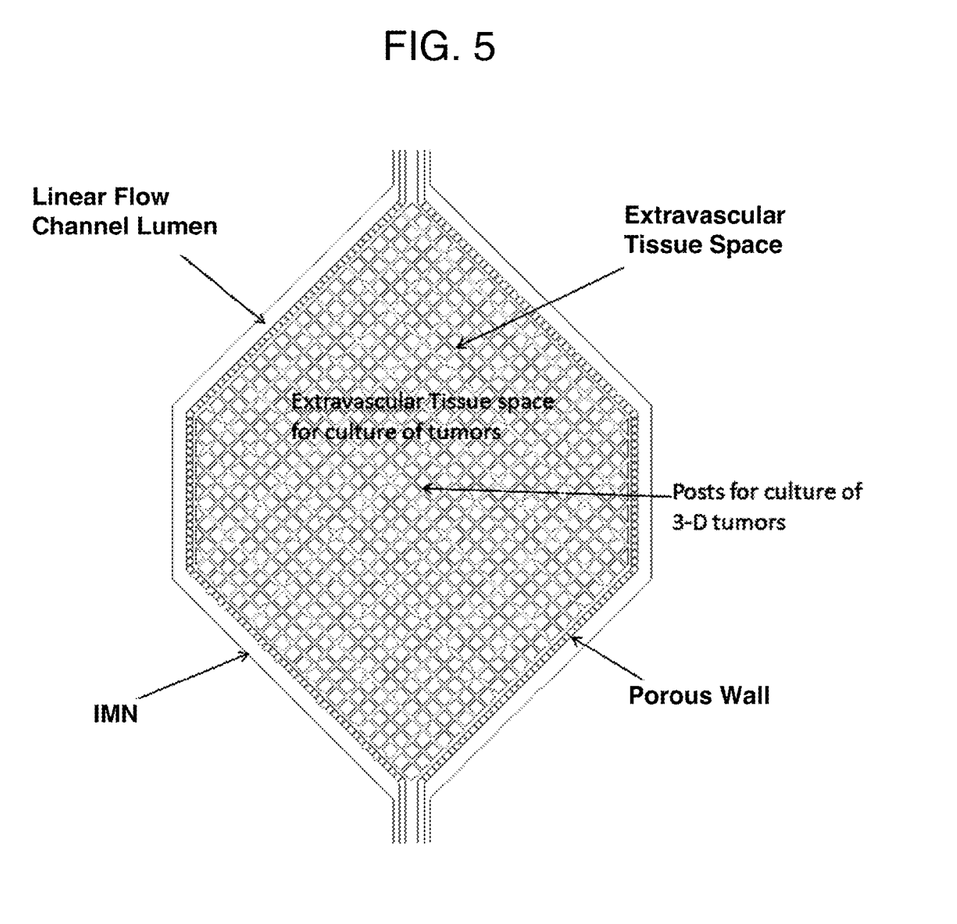
FIG. 5 is a drawing showing an IMN on a microfluidic chip for growing tumor cells to simulate a 3-dimensional solid tumor.

FIG. 4 shows a portion of an IMN in a microfluidic chip. In this example, an extravascular tissue space is surrounded by linear flow channels. The walls of the linear flow channels contain gaps, preferably from 0.2 μm to 5 μm wide, or pores, preferably from 0.2 μm to 5 μm in diameter, that allow fluid to diffuse from the flow channels into the tissue space. FIG. 5 shows a portion of an IMN comprising an extravascular tissue space that contains posts configured to facilitate the growth of adhesion dependent tumor cells to for a 3-dimensional solid tumor. While the network in this example is an IMN, 3-dimensional solid tumors may be grown in SMNs as well. Although the microfluidic chips and microvascular networks of the invention are largely planar, the depth of tissue spaces and the inclusion and arrangement of posts or other scaffolds within the tissue spaces can be designed to produce tumor cell monolayers and bilayers, as well as 3-dimensional solid tumors. The location of each tissue space in the network may be selected by the user. However, in the case of tumor vasculature derived from images using techniques such as intra-vital microscopy, the locations of tissue spaces are kept the same as observed in-vivo.

Figure 6:
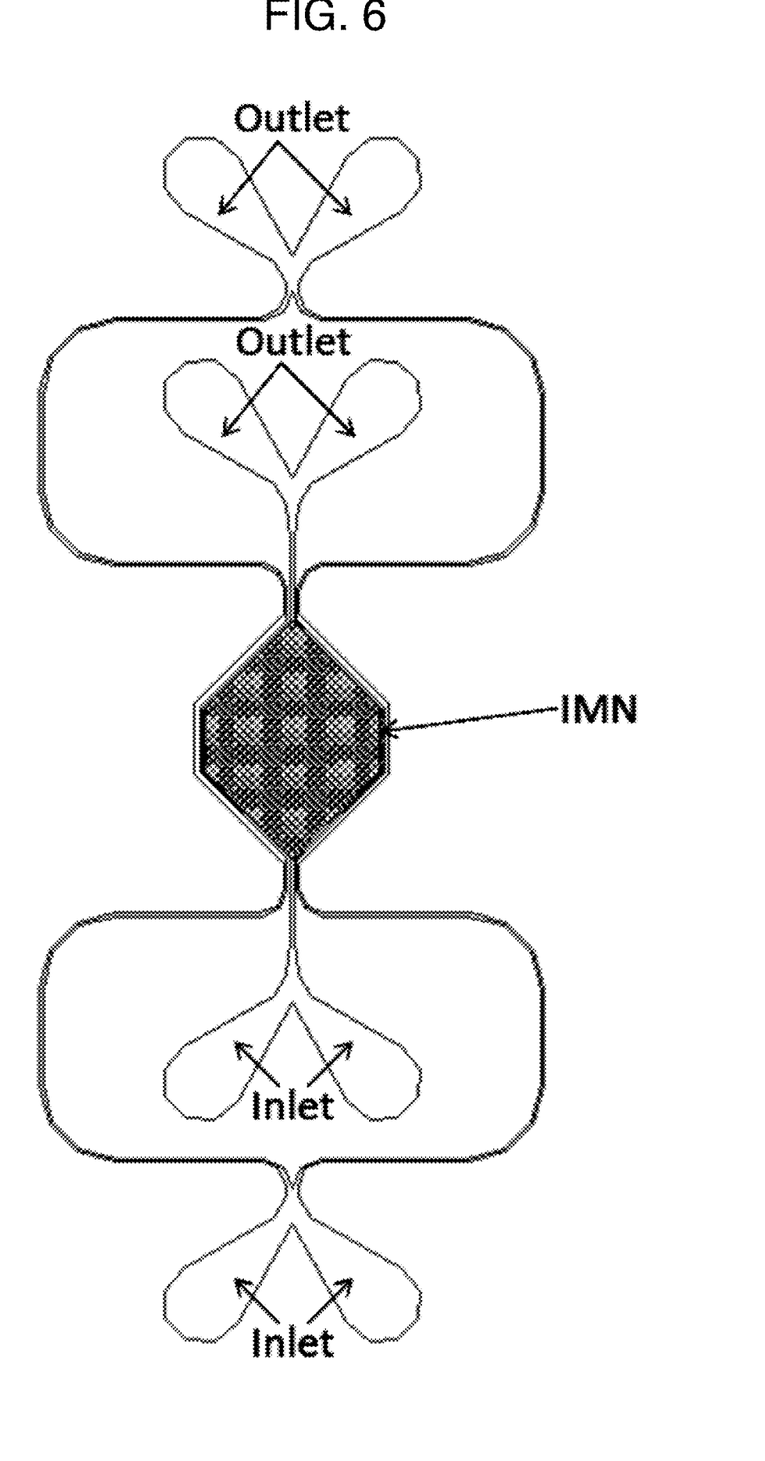
FIG. 6 is a drawing showing the components of a microfluidic chip used for screening tumor drug delivery vehicles using an IMN.
Figure 7:
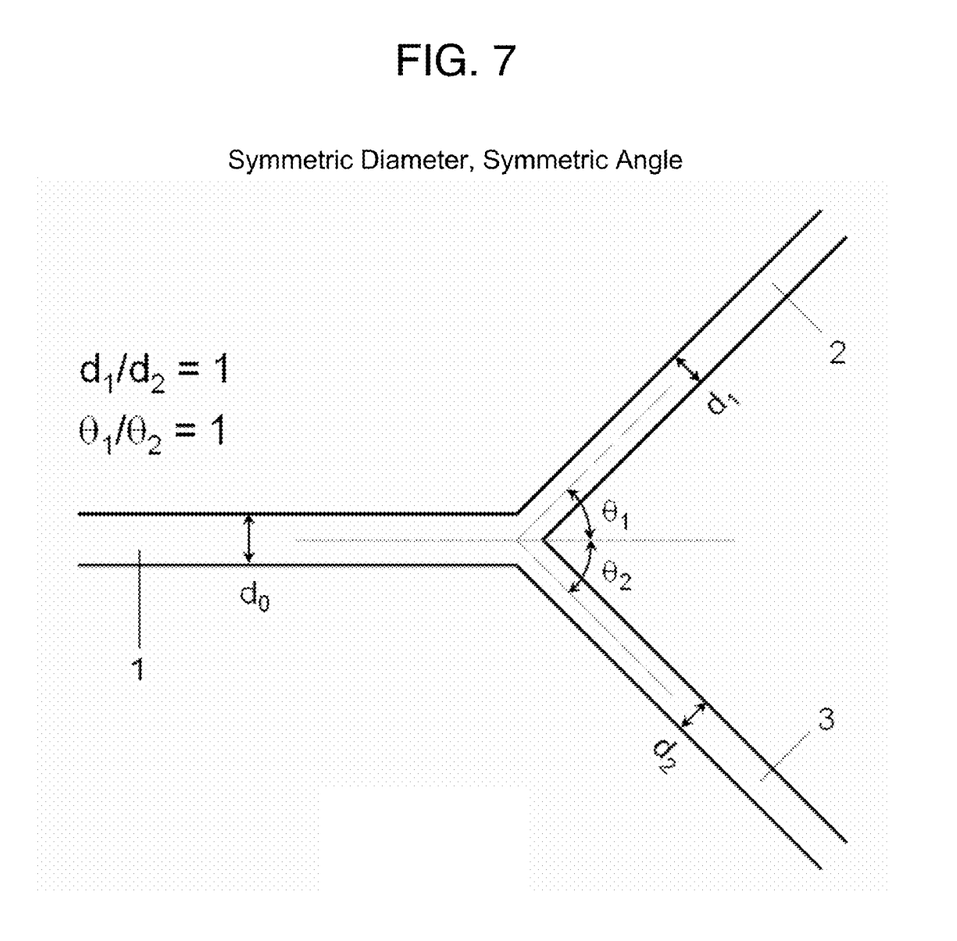
FIG. 7 shows a symmetric bifurcation with symmetric daughter diameters.
Figure 8:
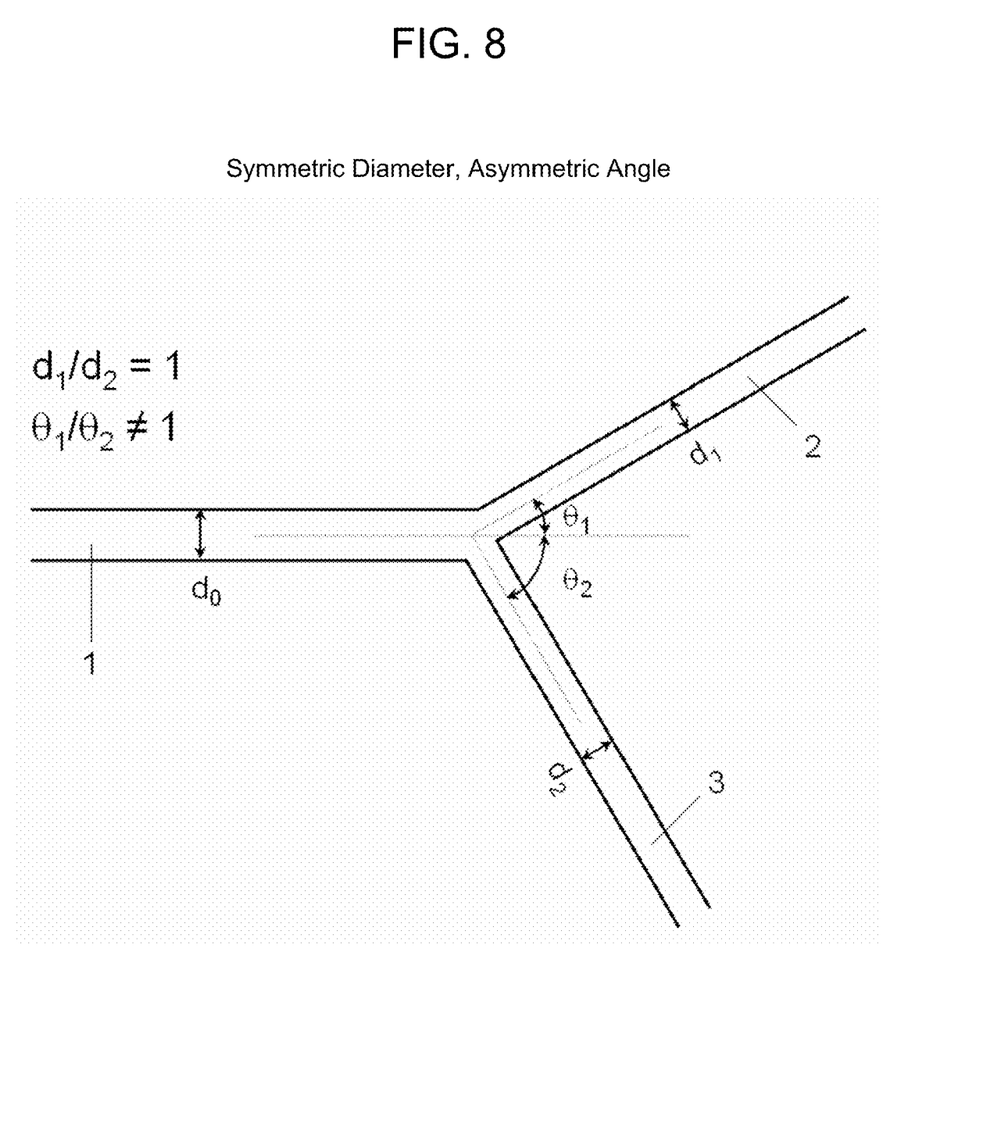
FIG. 8 shows an asymmetric bifurcation with symmetric daughter diameters.
Figure 9:
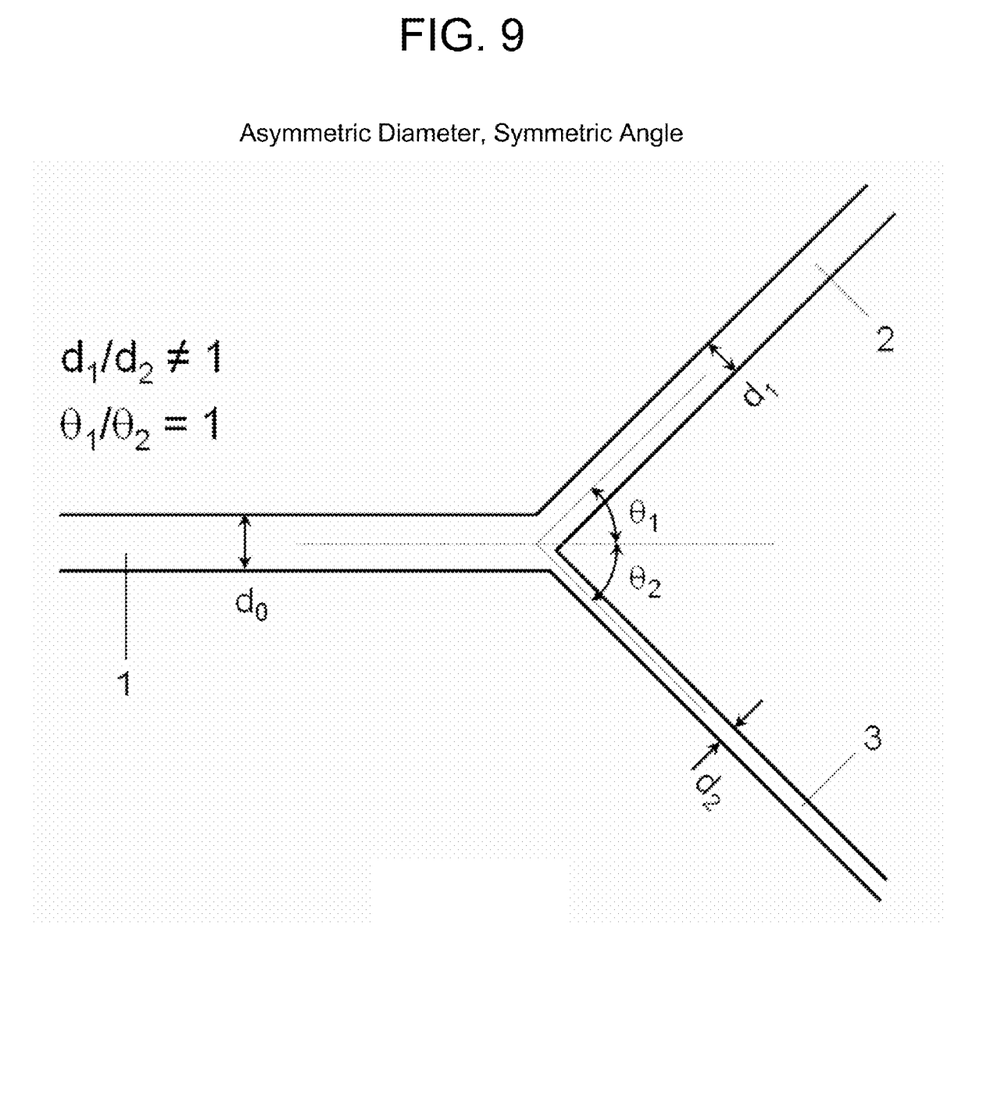
FIG. 9 shows a symmetric bifurcation with asymmetric daughter diameters.
Figure 10:
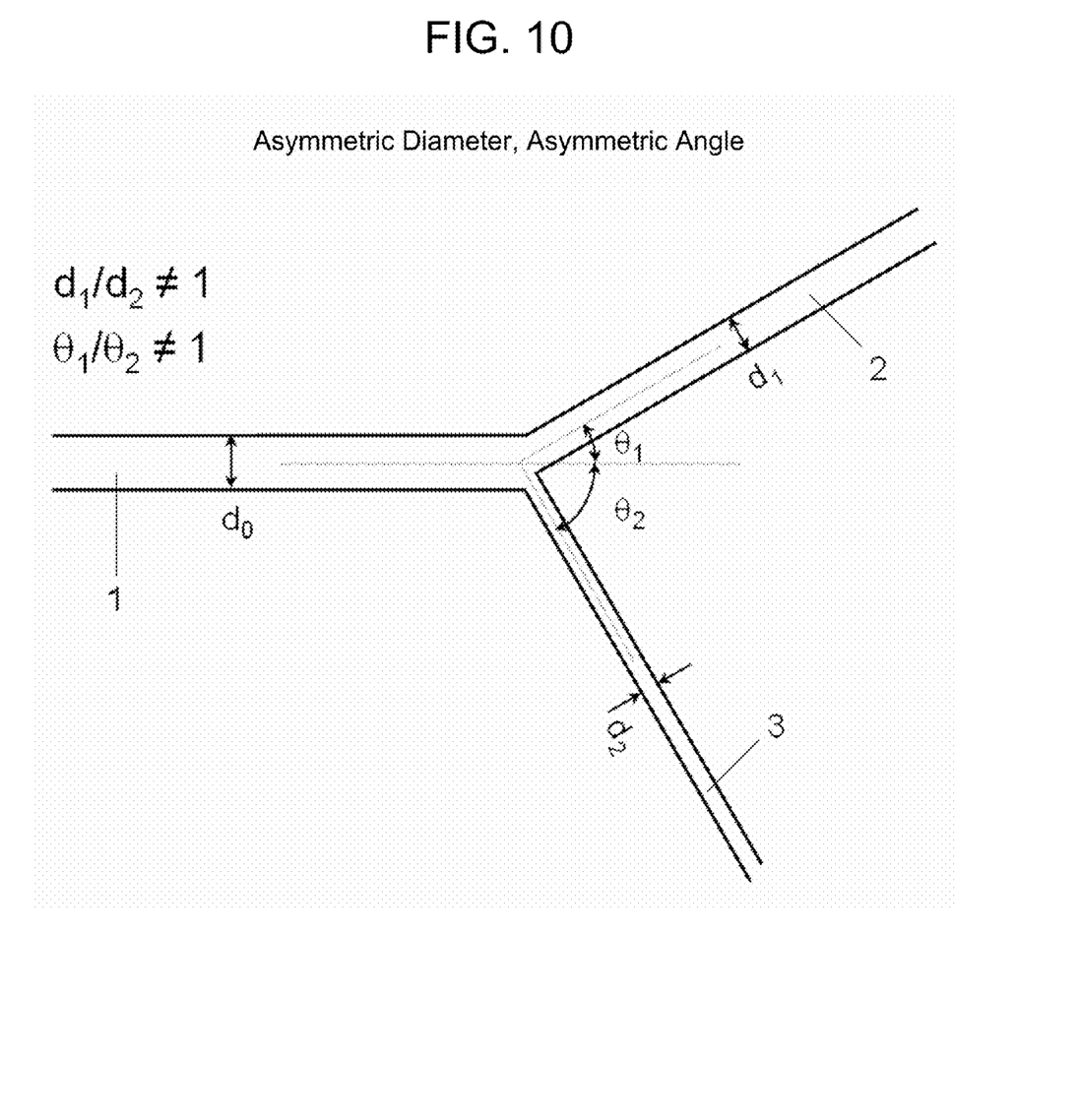
FIG. 10 shows an asymmetric bifurcation with asymmetric daughter diameters.

FIG. 6 shows an example of a microfluidic chip comprising an IMN, with a tissue space containing posts that serves as anchors to facilitate the formation of a 3-dimensional tumor. The IMN and the tissue space are each in fluid communication with a fluid inlet and a fluid outlet. Separate dedicated inlets and outlets for the IMN and the tissue space allow fluid to be pumped through both the IMN and the tissue space. Fluid flows through the inlet and outlet of the IMN can be controlled to maintain specified flow rates and shear rates, for example. Fluid flow and/or pressure applied through the inlet and outlet of the tissue space may be controlled to maintain a simulated interstitial pressure or to simulate lymphatic drainage.

Obtaining Geometries for SMNs:

The geometries for SMNs are derived from physiological microvascular networks. A geometry may, for example, be an exact replica of a digitized image of a natural microvascular network or an average of several digitized images. Maps of complete microvascular networks are constructed from a collage of arterioles, capillaries and venules. An entire network is digitized by tracing each vessel on the assembled collage in AutoCad Map® using a computerized drawing board such as Drawing Board III®, CalComp.

After a network is digitized, an AutoCad Map® cleanup routine is used to ensure all vessels are properly connected at their common nodes. A tolerance value is set which distinguishes between common nodes and neighboring end points. Each vessel is graphically represented by a polyline consisting of a series of straight lines connected through vertices. The routine compares the distances between successive vertices in a polyline to the set tolerance value. The vertex is removed from the polyline if the distance is below the set tolerance value. Tumor vascular structures can be obtained using intra-vital microscopy techniques and animal models, such as dorsal skin window models and open brain model in rodents. Additional methods of imaging tumor microvasculature include digital photographs of tumor microvascular networks.

Reconstructed "Averaged" Microvascular Networks:

Averaged or nominal micovascular networks are based on the geometries of at least two actual physiological microvascular networks. The images are analyzed as described above and subjected to a detailed morphological analysis to yield statistical data of morphometric parameters such as ratios of parent to daughter vessel diameters, branching angles, distances between branches, rations of branch length to branch channel diameter, tortuosity, bifurcation branch density, and recombining branch density. Averaged microvascular networks can be generated by using averaged morphometric data and/or stochastic sampling of probability density functions for morphometric data. Averaged microvascular networks may be generated using values selected from a variety of statistical distributions for individual morphometric parameters. The values used need not be "average," "mean," or "median" values for measured morphometric parameters.

Idealized Microvascular Networks (IMNs)

Idealized microvascular networks comprise single or multiple bifurcations and/or junctions consisting of linear parent and daughter channels having rectangular or circular or semi-circular cross-sections that diverge or converge at angles of between 15° and 135°. The diameters or cross-sections of the channels are between 10 μm and 500 μm. The bifurcations and junctions are categorized as illustrated in FIG. 7 through FIG. 10. In the figures, $d_0$, $d_1$, and $d_2$ represent the diameters of the parent (1) and first and second daughter channels (2, 3), respectively. $\theta_1$, and $\theta_2$ represent the angles formed between the parent channel (1) and the first and second daughter channels (2, 3), respectively. "Diameter" in the context of channels having a rectangular cross-section refers to the longest cross-sectional distance and cross-sectional area is calculated as width×depth. For channels having circular cross-sections, cross-sectional area is calculated as diameter×diameter×π/4. For channels having semi-circular cross-sections, "diameter" refers to the longest cross-sectional dimension and cross-sectional area is calculated as diameter×diameter×π/8.

Microfluidic Chip Fabrication:

Microvascular network structures obtained from in-vivo animal data as for SMN or averaged or idealized microvascular networks (IMN) are patterned onto an optically clear plastic such as PDMS (polydimethylsiloxane) using conventional soft lithography/replica casting techniques and as described in U.S. Ser. No. 11/393,715 to form a SMN. CAD drawings of physiological networks are modified to include gaps in the walls of the vessels. The patterns of these vessels include tissue sections including selected locations ranging from one to the entire tissue space comprising wall sections with gaps with dimensions between 0.2 μm to 5 μm. When fabricated using PDMS, the aspect ratio of these structures should be maintained such that the length (or width) of the structure is greater than twice the channel depth. For 25-50 μm channel depth, this places a minimum requirement on the structure length (and width) of 50-100 μm. The structures are optimally at least 50×50 μm in size. The flow channels may be covered with extracellular matrix components such as fibronectin, collagen, integrins, and other proteins and proteoglycans. Endothelial cells are cultured on the luminal side of the flow channels and tumor cells are cultured in the tissue space(s).

A similar approach is used to fabricate the IMN with gaps with dimensions between 0.2 μm to 5 μm. As before endothelial cells are cultured on the luminal side of the flow channels and tumor cells are cultured in the tissue spaces.

Endothelial cells from any source can be cultured in the vascular channels. Similarly tumor cells from any source, whether adherent and suspension, can be cultured in the tumor space Culture of Endothelial Cells and Tumor Cells:

Sterile phosphate buffer saline is injected into a SMN or an IMN at a flow rate of 10 μl/min for 10 minutes using a syringe pump to prime the device. Extracelluar matrix (e.g. fibronectin, gelatin, collagen) at a concentration of 50 μg/ml and flow rate of 10 μl/min is introduced into the chamber for 5 minutes. Flow is stopped and fibronectin solution is allowed to incubate for 2 hrs at room temperature to completely saturate the surfaces. Endothelial cells at a concentration of $5 \times 10^3$ to $5 \times 10^7$ cells/ml are introduced into the chamber with media and allowed to incubate for 4 hours. Media is replaced every 24 hours until the cells are confluent (>80%) in the network.

The extracellular tissue spaces are coated with basement membrane matrix such as Matrigel® (BD Biosciences, Bedford, Mass.). Tumor cells are resuspended at a concentration of $5 \times 10^3$ to $5 \times 10^7$ are mixed with Matrigel® to a final concentration of 0.1 to 1 mg/ml. This mixture is injected into the tissue spaces of the network and allowed to equilibrate in an incubator at 37° C. and 5% $CO_2$ overnight. The microfluidic chip is placed on an automated stage mounted on an inverted microscope equipped with a camera and imaging software.

Transport and Stability Studies of the Delivery Vehicles:

A common feature attributed to the ineffectiveness of polymer-based delivery vehicles is aggregation in the presence of serum proteins under flow conditions. This aggregation leads to reduced diffusion and ability to deliver drug to the tumor. This procedure provides a non-limiting example of a method for analyzing the stability and transport efficiency of a drug delivery vehicle.

Figure 11:
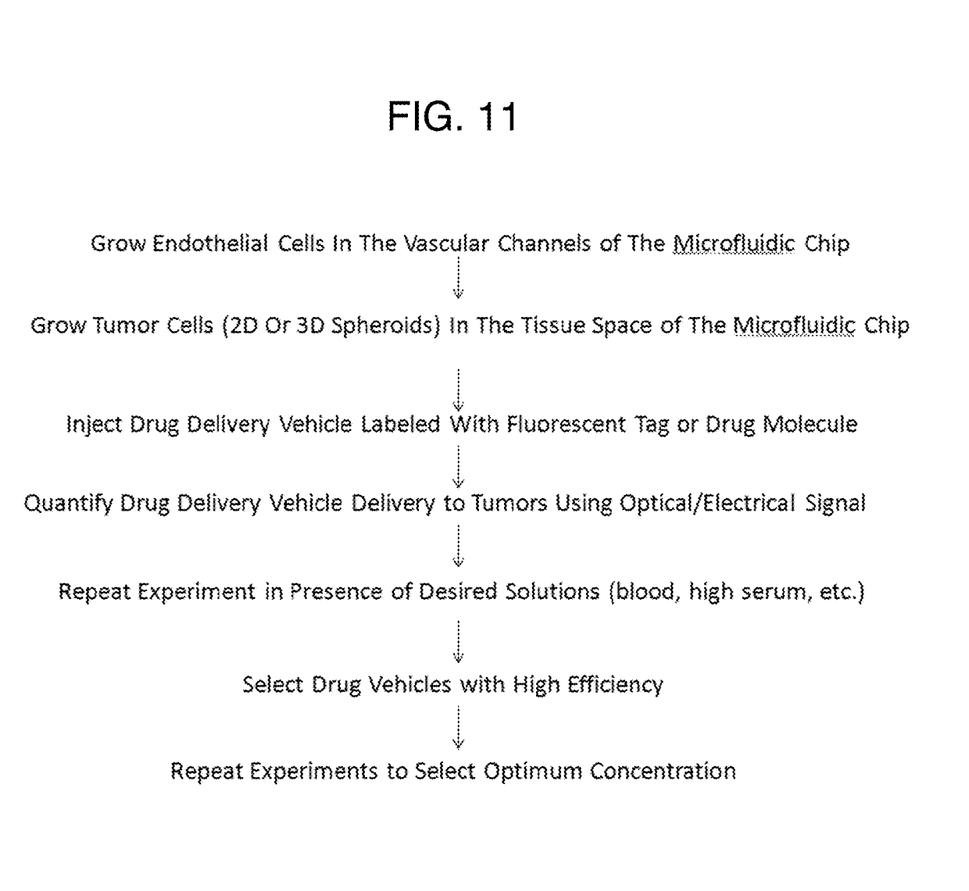
FIG. 11 is a flow chart showing method steps for screening one or more drug delivery vehicles for tumor drug delivery.

Drug delivery vehicles (fluorescently tagged) are introduced into the network inlet at a shear rate at the inlet arm of the network of 500 sec-1 using a peristaltic pump or a syringe pump. A range of shear rates from 0-500 sec-1 is established in the network and the flow rate is maintained in circulation for 4 hours. Every 30 minutes, the network is scanned to assess the fluorescent intensity in the tissue space of the device. A higher intensity of the drug delivery vehicle indicates maximal transport of the vehicles to the tumor location. Degradation of the delivery vehicles is monitored in the flow channels by analyzing loss of intensity of circulating vehicles and aggregation is monitored by visualization of clumping of delivery vehicles. Concentrations of the delivery vehicles and shear rate are varied to determine the affects of concentration and shear rates on stability, aggregation, and delivery. The experiment is repeated with the drug delivery vehicles suspended in whole blood, apheresed blood, and in media containing white blood cells, red blood cells and/or platelets. FIG. 11 shows general method steps for screening one or more drug delivery vehicles for tumor drug delivery.

Complex flow in the device may be characterized experimentally or using computational fluid dynamics (CFD) simulations in advance of the assay and stored in a database. The experiment may be repeated using flow rates corresponding to different shear rates or the device can be designed to incorporate regions providing different shear rates at the same flow rate at the inlet or inlets to allow data collection at varying shear rates.

Analyzing Gene Delivery by the Delivery Vehicles:

Candidate drug delivery vehicles tagged with a fluorescent protein expression gene are introduced into the inlet of a microfluidic device at shear rate of 500 sec-1. A single pass of delivery vehicle is utilized using a syringe pump or they are maintained in circulation using a peristaltic pump for 24 hour. Every 2 hours, the entire network is scanned and stitched to locate the areas of GFP expressing tumor cells. GFP expression is compared with a control lacking the GFP gene as an indicator delivery vehicle success. Similar to the previous assay, concentrations and shear rates can be varied.

Analyzing Drug Delivery by Delivery Vehicles:

A drug coupled to a candidate delivery vehicle is injected into the inlet of the microfluidic device at a shear rate of 500 sec-1. Every 2 hours, the entire network is scanned to assess tumor growth in one or more tissue spaces. A reduction in tumor size indicates that the drug is delivered to the tumor.

Tumor growth may be assessed visually and/or electronically. Electrodes may be incorporate into opposing walls of one or more tissue spaces. Tumor cell growth acts as an insulating barrier between the two electrodes. In response to drug delivery to the tissue space, tumor cells die, resulting in a modulation of impedance across the tissue space. Drug delivery vehicles such as nanopolymers, Qdots and other biological or synthetic vehicles can be readily tested.

While the invention is directed primarily toward tumor drug delivery, the methods and apparatus described herein may be altered to assay for drug delivery to other tissues without departing from the spirit of the invention. For example, tissue spaces may contain cells that are not derived from tumors such as non-neoplastic primary cell cultures and cell lines that are transformed to contain recombinant genes. The pore size of porous flow channel walls may also be modified to mimic diffusion across other physiological barriers, including the blood-brain barrier and linings of the small intestine.

The invention claimed is:

1. An optically transparent microfluidic chip comprising:
a) a network of nonlinear, interconnected flow channels in fluid communication with a network inlet and a network outlet, said flow channels having luminal cross-sectional dimensions of between 10 and 500 μm, the network of non-linear, interconnected flow channels having a geometric characteristic selected from the group consisting of a variable cross-sectional shape, a variable cross-sectional area, a turn, a bend, a bifurcation, a junction, a convolution, an anastomosis, and combinations thereof; and
b) a tissue space in fluid communication with a tissue space inlet and a tissue space outlet, said tissue space having cross-sectional luminal dimensions of between 100 μm and 1 cm
wherein:
the tissue space is separated from a lumen of at least one flow channel by a porous wall containing pores or gaps having cross-sections of between 0.2 and 5 microns and is in liquid communication with said flow channel through said porous wall and
the tissue space contains cultured cells.

2. The microfluidic chip of claim 1, wherein the interconnected flow channels form a synthetic microvascular network or an idealized microvascular network.

3. The microfluidic chip of claim 1, wherein the geometry of the synthetic microvascular is identical to a digitized physiological microvascular network or an average of two or more digitized physiological microvascular networks.

4. The microfluidic chip of claim 1, further comprising one or more ports configured to allow fluid to enter and/or exit a lumen of the tissue space.

5. The microfluidic chip of claim 1, wherein the pores or gaps are filled with a substance selected from the group consisting of a gel, a basement matrix, an extracellular matrix, a tissue matrix, a synthetic matrix, a natural matrix, polymer and combinations thereof.

6. The microfluidic chip of claim 1, wherein luminal surfaces of the flow channels are coated with a layer of cells.

7. The microfluidic chip of claim 1, wherein luminal surfaces of the flow channels are coated with a substance selected from the group consisting of a protein, a proteoglycan, a chemical moiety, a biomolecule, and combinations thereof.

8. The microfluidic chip of claim 1, wherein the tissue space contains a first type of tumor cells and, optionally, one or more of endothelial cells, epithelial cells, endothelial cells, fibroblasts, bone marrow cells, embryonic cells, hepatocytes, myocytes, neural cells, adipocytes, and a second type of cultured tumor cells.

9. The microfluidic chip of claim 1, wherein cultured endothelial cells are present on the interconnected flow channels.

10. The microfluidic chip of claim 1, further comprising a buffer solution in the lumen of the interconnected flow channels and the lumen of the tissue space.

11. The microfluidic chip of claim 1, wherein the tissue space is separated from the lumen of two or more flow channels by porous walls and is in liquid communication with said flow channels through said porous walls.

12. The microfluidic chip of claim 1, further comprising a valve in fluid communication with the lumen of the tissue space, said valve configured to regulate pressure inside the tissue space.

13. The microfluidic chip of claim 1, wherein the cells contained in the tissue space are present in a form selected from the group consisting of a monolayer, a bilayer, a three-dimensional cluster, and combinations thereof.

14. An apparatus comprising the microfluidic chip of claim 1; pumping means configured to move fluid from the network inlet to the network outlet; and optical detection means configured to visualize and quantitate cells, drug delivery vehicles and drugs.

15. A method for assaying a drug delivery vehicle comprising the steps of:
providing the optically transparent microfluidic chip of claim 1;
introducing a liquid containing a drug delivery vehicle and drug into the network inlet of the optically transparent plastic microfluidic chip;
causing the liquid containing the drug delivery vehicle and the drug to move though the network of interconnected flow channels; and
quantifying the amount of the drug reaching the tissue space, the cells, or both.

16. The method of claim 15, wherein the cells contained in the tissue space are selected from the group consisting of primary tumor cells, a cultured tumor cell line, transformed cells, and combinations thereof.

17. The method of claim 16, wherein the tissue space additionally contains cells selected from the group consisting of endothelial cells, epithelial cells, fibroblasts, bone marrow cells, neuronal cells, hepatocytes, myocytes, adipocytes, embryonic cells, and combinations thereof.

18. The method of claim 15, wherein the cells contained in the tissue space are present in a form selected from the group consisting of a monolayer, a bilayer, a three-dimensional cluster, and combinations thereof.

19. The method of claim 15, wherein the tissue space additionally contains one or more of an extracellular matrix, a basement membrane, a synthetic matrix, and a natural occurring matrix.

20. The method of claim 15, wherein quantifying the amount of the drug is performed by a means comprising optical or electrical detection.

21. The method of claim 15, wherein the drug delivery vehicle is selected from the group consisting of: a cells, a liposome, a lipisome, a lipoprotein, a microencapsulated drug, a particulate drug carrier, a nanoparticle, a micropar-ticle, nanocrystals, a polymer bead, a virus, and a bacterium.

22. The method of claim 15, wherein the liquid containing a drug delivery vehicle and a drug is moved through the network of interconnected flow channels once, multiple times or is recirculated for a desired time or a combination of all through the network of interconnected flow channels using electrokinetic forces, pumps and/or other driving mechanisms.

23. The method of claim 15, wherein the drug is attached to the drug delivery vehicle and the drug is selected from the group consisting of: a native gene; a recombinant gene a naturally occurring compound, and a synthetic compound.

24. The method of claim 15, wherein a liquid containing a plurality of drug delivery vehicles and a plurality of drugs is introduced into the network inlet.

25. The method of claim 15, and further comprising the method step of measuring a property of the drug delivery vehicle, said property selected from the group consisting of: real-time circulation, stability, half life, rate of aggregation, rate of degradation and combinations thereof.

26. The method of claim 15, wherein the liquid is moved through the network of interconnected flow channels with varying fluidic shear rate values of between 1 se-1 and 2000 sec-1, as measured experimentally or predicted by computational simulation.

27. The method of claim 15, wherein the liquid is selected from the group consisting of: a cell culture media, a buffer containing serum proteins, whole blood, apheresed blood a buffer containing leukocytes, a buffer containing erythrocytes, and a buffer containing platelets or combinations thereof.

28. The method of claim 15, wherein said plurality of interconnected flow channels forms a synthetic microvascular network.

29. The method of claim 15, wherein said plurality of interconnected flow channels forms an idealized microvascular network.

30. The method of claim 1 wherein said porous wall comprises pores or gaps having maximal cross-sections of between 0.2 and 5 microns.

* * * * *